United States Patent [19]

Kane et al.

[11] Patent Number: 4,570,642
[45] Date of Patent: Feb. 18, 1986

[54] ENDOCARDIAL EXTENDABLE SCREW-IN LEAD

[75] Inventors: Lawrence M. Kane, Roseville; James E. Revane, Minnetonka, both of Minn.

[73] Assignee: Daig Corporation, Minnetonka, Minn.

[21] Appl. No.: 535,318

[22] Filed: Sep. 23, 1983

[51] Int. Cl.[4] ............................................... A61N 1/04
[52] U.S. Cl. ................................ 128/785; 128/419 P
[58] Field of Search ............................... 128/784-786, 128/642, 419 P

[56] References Cited

U.S. PATENT DOCUMENTS

| 4,106,512 | 8/1978 | Bisping .................... 128/419 P X |
| 4,146,036 | 3/1979 | Dutcher et al. ................ 128/785 |
| 4,217,913 | 9/1980 | Dutcher ...................... 128/785 |
| 4,463,765 | 8/1984 | Gold ......................... 128/785 |

FOREIGN PATENT DOCUMENTS

| 2806069 | 8/1979 | Fed. Rep. of Germany ...... 128/785 |
| 882529 | 11/1981 | U.S.S.R. ....................... 128/785 |

Primary Examiner—Lee S. Cohen
Attorney, Agent, or Firm—Williamson, Bains, Moore and Hansen

[57] ABSTRACT

An intravascular endocardial lead includes an electrically insulated flexible conductor having a lumen throughout the length thereof. A hollow connector element is connected to the proximal end of the conductor, and a hollow elongate electrode is connected to the distal end thereof. A helix assembly is positioned in the electrode and is longitudinally but non-rotatably movable from a retracted position to an extended position. A stylet is inserted through the lumen of the conductor to move the helix assembly to the extended position. Thereafter, when the conductor, electrode and helix assembly are rotated as a unit about the stylet, the helix assembly will penetrate and positively attach the lead to the body tissue and urge the electrode into engagement with the latter.

6 Claims, 3 Drawing Figures

U.S. Patent  Feb. 18, 1986  4,570,642
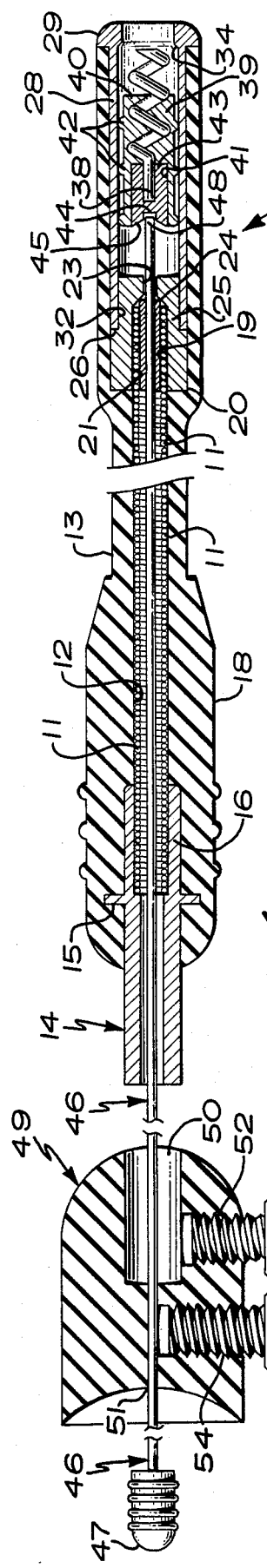
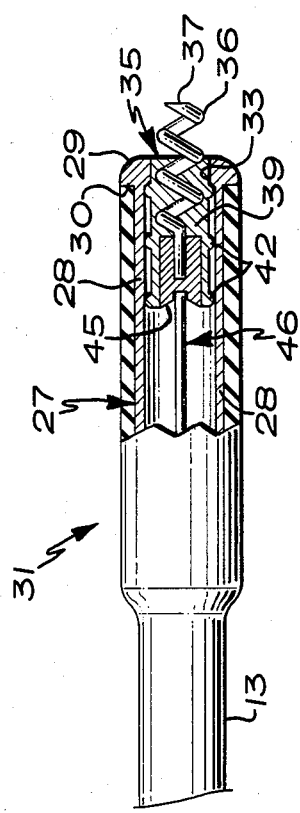
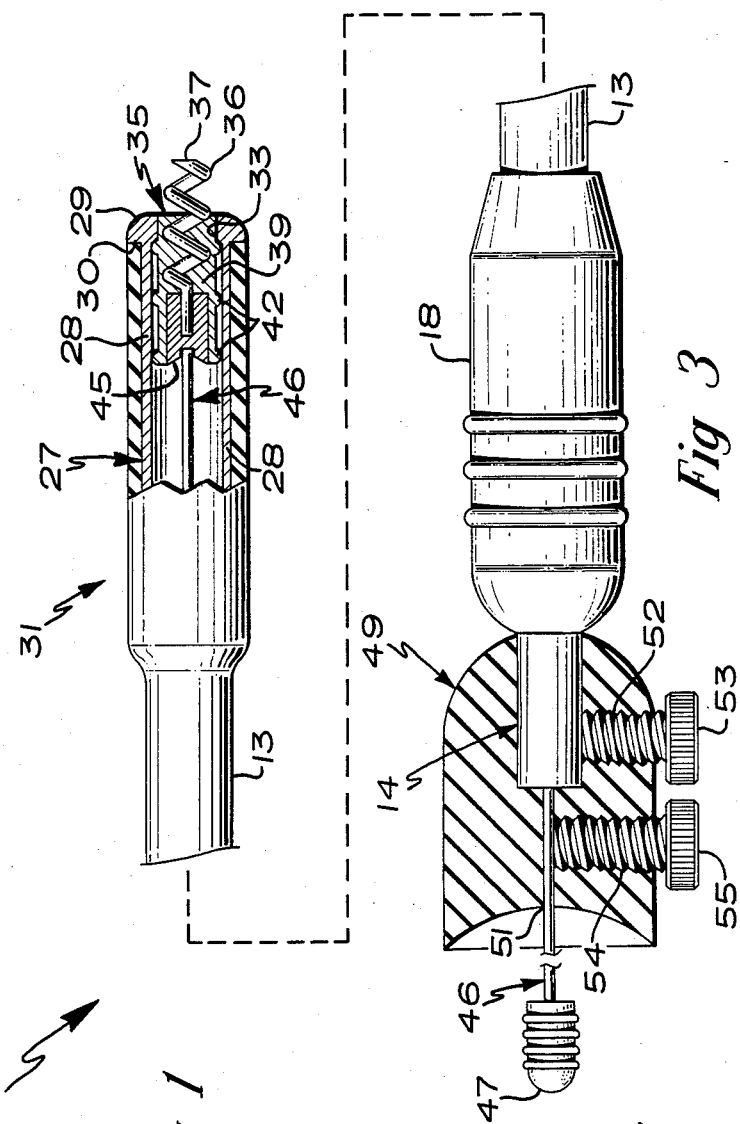
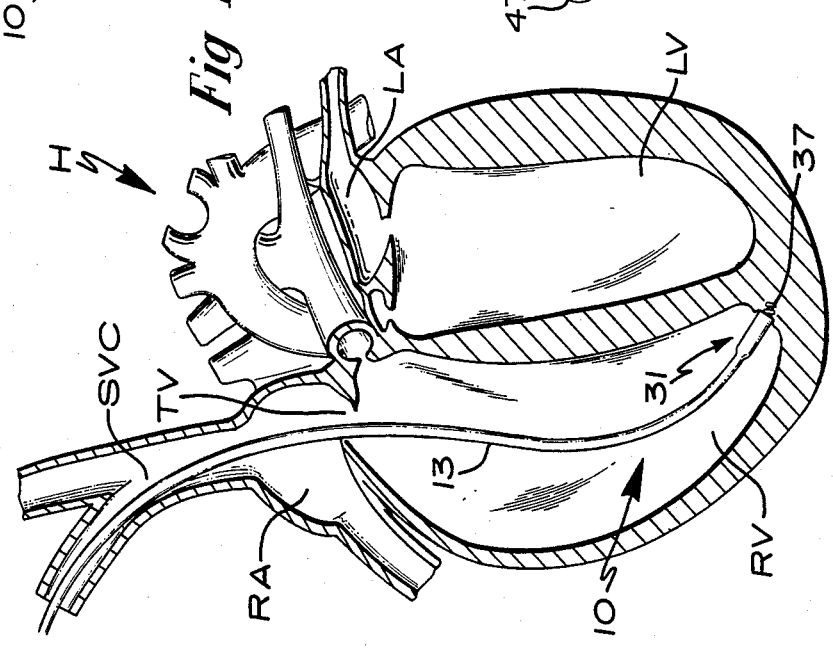

ENDOCARDIAL EXTENDABLE SCREW-IN LEAD

BACKGROUND OF THE INVENTION

This invention relates to an electrical lead for connecting animal tissue to an electrical stimulation generator, and more particularly to an endocardial lead having a retractable helix for fixation to the cardiac tissue.

The screw-in concept has long been known as a viable means for achieving positive fixation in atrial and ventricular pacing applications. However, certain drawbacks do exist in the current state of the art devices, such as overall size, exposed fixation means, fluid leakage and point of stimulation being remote from point of fixation. At the present time, it appears that no one design has been able to overcome all of these drawbacks.

SUMMARY OF THE INVENTION

It is the general object of this invention to provide an intravascular endocardial lead with a corkscrew fixation element which is retracted within the electrode for ease of passage through the vein and which is thereafter extended for active fixation in either the atrial or ventricular chambers.

A further object of this invention is to provide a novel and improved intravascular endocardial screw-in lead which, when fixed to the cardiac tissue, substantially reduces electrode micromovement and the resulting development of fibrotic tissue build-up so that acceptable chronic pacing and sensing thresholds are maintained.

Another object of this invention is to provide a novel and improved intravascular endocardial lead having a corkscrew fixation element mounted within the electrode by a sealing member which prevents accidential dislodgment of the corkscrew element and provides a positive seal to prevent fluid leakage.

These and other objects and advantages of the invention will appear more fully from the following description made in conjunction with the accompanying drawings wherein like reference characters refer to the same or similar parts throughout the several views.

FIGURES OF THE DRAWING

FIG. 1 illustrates the novel lead permanently secured to the tissue of the right ventrical of the heart;

FIG. 2 is a side view, partly in section and partly in elevation and foreshortened for clarity, illustrating the screw-in fixation element in a retracted position; and FIG. 3 is a side view, partly in section and partly in elevation and foreshortened for clarity, of the lead illustrating the fixation element in an extended position.

DESCRIPTION OF THE PREFERRED EMBODIMENT

Referring now to the drawings, it will be seen that one embodiment of the novel intravascular endocardial lead, designated generally by the reference numeral 10, is thereshown. Although the lead 10 is illustrated as a unipolar lead, it may be of a unipolar or bipolar configuration, and comprises a flexible, insulated catheter including a coil conductor 11 formed of nickel alloy wire. The coil conductor defines a lumen 12 and the conductor is covered with a sleeve or jacket 13 of electrically insulating material, namely silicone rubber.

The proximal end of the conductor 11 is connected to a tubular connector pin 14 which is adapted for insertion in a receptacle provided on the pulse generator with which the lead is used. It will be noted that the connector pin 14 is embedded in the silicone catheter sleeve 13 and projects therefrom. The connector pin 14 is also provided with a radial collar 15 intermediate its ends for firmly anchoring the connector pin 14 in the enlarged proximal end portion 18 of the insulator sleeve 13. The connector pin 14 includes a front portion 16 into which projects the coil conductor 11.

The distal end of the coil conductor 11 projects into the cylindrical bore 19 of element 20. The distal end of the conductor 11 is positioned exteriorly around a tube 21 and is secured to the element 20. It will be noted that the bore 19 through the element 20 is uniform in size throughout the major portion of its length, but is provided with a reduced end portion 23 at the distal end thereof. The reduced end portion of the bore defines an annular beveled shoulder 24.

The element 20 also has a reduced distal end 25 that defines an annular shoulder 26 against which one end of an elongate ring tip electrode 27 bears. The ring tip electrode 27 is preferably formed of platinum iridium alloy, and includes an elongate cylindrical sleeve or barrel 28 provided with an outwardly projecting annular lip 29 at its outer end. The proximal end of the barrel is affixed to the element 20 which is formed of electrical conductive material. It will therefore be seen that the electrode 27 is electrically connected by means of the element 20 to the conductor 11. The outwardly projecting lip 29 defines a rearwardly facing shoulder 30, and it will be seen that the entire electrode assembly, with the exception of the annular ring shaped lip 29, is covered by the enlarged distal portion 31 of the silicone rubber catheter sleeve 13. The ring or lip 29 at the distal end of the electrode contacts the endocardium when the lead is attached.

The interior 32 of the barrel 28 is uniformly cylindrical, but is reduced, as at 33, at its distal end. The reduced end 33 of the opening defines an annular beveled shoulder 34. A helix assembly 35 is positioned within the barrel 28 and is movable longitudinally therein from a retracted position, as illustrated in FIG. 2, to an extended position, as illustrated in FIG. 3.

The helix assembly 35 includes a corkscrew or helical element 36, which is also formed of platinum iridium material, and which has a point 37 at its distal end and a straight, proximal end portion 38. It will be seen that an intermediate portion of the corkscrew 36 is imbedded in a cylindrical sealing member 39, which is formed of silicone rubber, so that the distal portion of the corkscrew projects axially from the distal planar end 40 of the sealing member. The rear end of the sealing member has a rearwardly facing, axially extending recess 41 therein.

The sealing member 39 is also provided with a plurality of axially spaced apart, annular sealing elements 42 which project radially outwardly therefrom. In the embodiment shown, three such sealing elements are provided which are equally spaced apart, the rearmost of which is disposed co-extensively with the rear end of the sealing member. It will also be noted that the forwardmost annular sealing element 42 is spaced rearwardly or proximally from the distal or forward face 40 of the sealing member 39. It will further be noted that the distance between the forwardmost annular sealing element 42 and the face 40 of the sealing member 39 corresponds to the axial dimension of the reduced opening 33 through the barrel 28.

The radial dimension of the annular sealing elements 42 are such that the sealing elements engage the inner surface 32 of the barrel 28 in sealing, frictional engagement. This frictional contact permits forcible longitudinal movement of the helix assembly but prevents rotation of the helix assembly relative to the electrode 27. It will also be noted that when the helix assembly is in the advanced or extended position, the forward or distally located annular sealing element engages the shoulder 34 of the barrel 28 to limit movement of the helix assembly in a distal direction.

The recess 41 in the sealing member 39 has a cylindrical helix metallic crimp or anchoring housing 43 affixed therein, the latter having a centrally located, rearwardly facing recess 44 therein. In this regard, it will be noted that the rear of the helix crimp housing 43 is beveled, as at 45, towards the recess 44. The straight, proximal end portion 38 of the corkscrew element 36 is embedded in the crimp housing 43 so that the corkscrew is not only embedded in the sealing member, but is also anchored in the crimp housing 43. With this arrangement, it has been found that the helix assembly cannot be forcibly pulled from the barrel 28 without first causing the helical element 36 to be straightened and hence release itself from the tissue in which it was affixed.

Means are also provided for shifting the helix assembly from the retracted position to the extended position, and this means includes an elongate stylet 46 formed of stainless steel wire and having a knob 47 at its proximal end. The stylet extends through the lumen 12 of the conductor 11, and through the tube 21 and into the barrel 28 and engages in the recess 44 of the crimp housing 43 for the helix assembly. The beveled surface 45 assists in seating the distal end 48 of the stylet in the recess 44 of the helix crimp housing 43.

A stylet spacer tool 49 is mounted on the proximal end of the lead 10 and comprises a housing having a recess 50 therein of a size to receive the connector pin 14 therein. The recess 50 communicates with a smaller bore opening 51 in the housing which is of a size to permit passage of the stylet 46 therethrough. The spacer tool housing is provided with a threaded recess or bore 52 therein which communicates with the recess 50. A metallic lead engaging screw 53 threadedly engages in the threaded recess 52. The housing is also provided with a threaded recess 54 therein adjacent the threaded bore 52, and the recess 54 communicates with the opening 51. A stylet engaging screw 55 threadedly engages in the threaded recess 54.

The connector pin 14 is positioned within the recess 50 and the lead engaging screw 52 is tightened thereagainst to detachably mount the stylet spacer tool 49 on the lead. The screw 55, when tightened, will engage the stylet 46 to retain the stylet in an adjusted position. The helix assembly may be moved by the stylet to the advanced or extended position to permit fixation of the lead to the cardiac tissue.

Referring again to FIG. 1, it will be seen that the lead 10 is illustrated in attached relation to the right ventricle of a heart. The heart H is shown in cross-section and includes the right atrium RA, the right ventricle RV, the left atrium LA and the left ventricle LV. It will be seen that the corkscrew has penetrated and is attached to the apex of the right ventricle. It will further be noted that the lead has been passed through the superior vena cava vein SVC, into the right atrium RA, through the tricuspid valve TV, and into the right ventricle RV.

In the procedure for attaching the lead to the cardiac tissue, the helix assembly will be in the retracted position and the distal end of the stylet will be moved forwardly until it merely engages the helix assembly. The screws 53 and 55 will be tightened to hold the spacer tool on the lead and to retain the stylet in a position of engagement with the helix assembly. After the distal end of the lead is passed into the chamber, the physician may now map the area of placement by connecting an oscilloscope or other monitoring device between the metal screw 53 on the stylet spacer tool 49 and ground. It will be appreciated that the screw 53 will be electrically connected to the coil conductor through the connector pin 14. Once an acceptable position for attachment is found, the plastic screw 55 on the stylet spacer tool 49 will be loosened thereby permitting the longitudinal movement of the stylet 46 relative to the lead 10.

The user will then hold the stylet spacer tool, which is tightened on the connector pin 14 of the lead, with one hand and will urge the stylet into the lead with the other hand a distance of approximately two to three inches. The distal end of the stylet will urge the helix assembly 35 longitudinally of the barrel until the helix assembly reaches the fully extended position, as illustrated in FIG. 3. The user will retain the stylet in this position until the helix is clearly visible on the fluoroscopy monitor. It is pointed out that the frictional contact between the annular sealing elements 42 provide a highly effective seal between the interior of the electrode barrel and the helix assembly, but permits longitudinal movement of the helix assembly relative to the barrel of the electrode. However, there is sufficient frictional contact between the annular sealing elements and the barrel to prevent rotation of the helix assembly relative to the barrel.

After the helix assembly has been moved to the extended position, the stylet 46 may now be retracted a few inches so that the distal end thereof is moved out of engagement with the helix assembly. The user will then tighten the screw 55 to retain the stylet in this retracted position. The user will then grip the stylet knob 47 with one hand and advance the stylet and lead as a unit forward slightly in order to make contact with the endocardium. The user then will grip the enlarged proximal portion 18 of the lead jacket and rotate the lead about the stylet in a clockwise direction approximately six turns to engage the endocardium with the corkscrew or helical element. The stylet retaining screw 55 will then be unloosened to permit the stylet to be retracted an additional three to four inches. Slight tension will then be applied to the lead 10 to verify fixation by observation with the fluoroscopy unit. Thereafter, the metal screw 53 will be loosened, and the stylet 46 and stylet spacer tool 49 will be removed.

Although the lead 10 is of unipolar configuration, it is pointed out that the present invention is intended to cover a bipolar lead, which incorporates the novel features. It is further pointed out that the present features can be incorporated in a J-atrial lead for atrial attachment. It will be appreciated that the lead 10 is intended primarily for use in a cardiac pacing system.

It has been found that when the insulated conductor, electrode and helix assembly are rotated as a unit about the stylet, the ring tip electrode 27 will be positively urged into contact with the endocardial tissue. In certain prior art leads the helix assembly is rotated relative to the electrode by a stylet in order to achieve fixation. While fixation is achieved with that type of prior art device, it has been found that positive contact of the electrode cannot be assured.

It has been found that when the insulated conductor, electrode and helix assembly are rotated as a unit about the stylet, the ring tip electrode 27 will be positively urged into contact with the endocardial tissue. In certain prior art leads, the helix assembly is rotated relative to the electrode by a stylet in order to achieve fixation. While fixation is achieved with that type of prior art device, it has been found that positive contact of the electrode cannot be assured.

Thus it will be seen that we have provided a novel lead for cardiac pacemakers which is a simple construction and which functions in a more efficient manner than any heretofore known comparable lead.

While the preferred embodiments of the present invention have been described, it should be understood that various changes, adaptions and modifications may be made therein without departing from the spirit of the invention and the scope of the appended claims.

What is claimed is:

1. An intravascular endocardial lead formed of a material inert to body fluids, comprising:
    an elongate, electrically insulated, flexible conductor having a lumen throughout the length thereof, and having proximal and distal ends,
    a connector element electrically connected to the proximal end of said conductor,
    an elongate, hollow electrode electrically connected to the distal end of said conductor and adapted to contact the endocardium,
    a helix assembly positioned in said electrode and including a sealing member formed of a yieldable, electrically non-conductive material engaging the interior of said electrode in fluid-sealing relation therewith, an elongate helical element having a proximal end portion secured to said sealing member and projecting distally therefrom, said helix assembly being longitudinally but non-rotatably shiftable from a retracted position wherein said helical element is disposed completely within the electrode, to an extended position wherein said helical element projects outwardly of the distal end of said electrode,
    an elongate stylet having proximal and distal ends and being inserted into the lumen of the conductor and engaging the helix assembly for shifting the same from the retracted position to the extended position whereby when said helix assembly is in the extended position and said conductor, electrode and helix assembly are rotated as a unit about said stylet, said helical element will penetrate the cardiac tissue and urge the electrode into positive engagement with the cardiac tissue.

2. The endocardial lead as defined in claim 1 wherein said sealing member has a plurality of spaced apart annular sealing elements integral therewith and extending radially outwardly therefrom engaging the interior of the electrode in sealing relation therewith.

3. The endocardial lead as defined in claim 1 wherein said connector element is of hollow construction, a spacer tool having an opening therethrough receiving the connector element of the lead therein, means on said spacer tool engaging said connector element releasably mounting the spacer tool on the latter, said stylet extending through the spacer tool and connector element into the lumen of the conductor, and stylet-engaging means on said spacer tool for releasably engaging the stylet to secure the spacer tool in nonmovable relation with respect to said stylet.

4. The endocardial lead as defined in claim 3 wherein said connector element engaging means on said spacer tool comprises a screw threadedly engaging in a threaded recess in said spacer tool.

5. The endocardial lead as defined in claim 1 wherein said sealing member of said helix assembly has a metallic crimp housing embeded therein, said helical element having one end thereof secured to said crimp housing, a recess in said crimp housing engaged by the distal end of said stylet when the latter engages and urges the helix assembly to the extended position.

6. The endocardial lead as defined in claim 1 wherein said electrode has an inwardly projecting lip at its distal end to define a rearwardly facing annular shoulder thereat, said sealing member engaging said shoulder when said helix assembly is in the extended position.

* * * * *